(12) United States Patent
Schmitt et al.

(10) Patent No.: US 11,576,637 B2
(45) Date of Patent: Feb. 14, 2023

(54) STANDARDIZED CORONARY ARTERY DISEASE METRIC

(71) Applicant: KONINKLIJKE PHILIPS N.V., Eindhoven (NL)

(72) Inventors: Holger Schmitt, Luetjensee (DE);
Hannes Nickisch, Hamburg (DE);
Manindranath Vembar, Twinsburg, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 169 days.

(21) Appl. No.: 16/500,215

(22) PCT Filed: Apr. 2, 2018

(86) PCT No.: PCT/EP2018/058376
§ 371 (c)(1),
(2) Date: Oct. 2, 2019

(87) PCT Pub. No.: WO2018/185040
PCT Pub. Date: Oct. 11, 2018

(65) Prior Publication Data
US 2020/0060637 A1 Feb. 27, 2020

Related U.S. Application Data

(60) Provisional application No. 62/557,195, filed on Sep. 12, 2017, provisional application No. 62/482,236, filed on Apr. 6, 2017.

(51) Int. Cl.
*A61B 6/00* (2006.01)
*G16H 50/50* (2018.01)
(Continued)

(52) U.S. Cl.
CPC .............. *A61B 6/504* (2013.01); *A61B 6/032* (2013.01); *G06T 7/0014* (2013.01); *G16H 50/50* (2018.01);
(Continued)

(58) Field of Classification Search
CPC ....... A61B 6/504; A61B 6/032; A61B 6/5217; G06T 2207/10081; G06T 2207/30104; G06T 7/0014; G06T 7/0016; G16H 50/50
See application file for complete search history.

(56) References Cited

U.S. PATENT DOCUMENTS 9,195,801 B1 11/2015 Sankaran
10,258,303 B2 4/2019 Grass
(Continued)

FOREIGN PATENT DOCUMENTS

WO WO2015150128 A1 10/2015
WO WO2016087396 A1 6/2016
WO WO20170221201 A1 2/2017

OTHER PUBLICATIONS

PCT International Search Report, International application No. PCT/EP2018/058376, dated Jun. 11, 2018.
(Continued)

*Primary Examiner* — Manuchehr Rahmjoo
(74) *Attorney, Agent, or Firm* — Larry Liberchuk

(57) ABSTRACT

A computing system (118) includes a computer readable storage medium (122) with computer executable instructions (124), including a biophysical simulator (126), and a reference location (128), and a processor (120) configured to the biophysical simulator and simulate a reference FFR value at a predetermined location along a segmented coronary vessel indicated by the reference location. A computer readable storage medium encoded with computer readable instructions, which, when executed by a processor of a
(Continued)

computing system, causes the processor to simulate a reference FFR value at a predetermined location along a segmented coronary vessel indicated by a predetermined reference location. A method including simulating a reference FFR value at a predetermined location along a segmented coronary vessel indicated by a predetermined reference location.

21 Claims, 5 Drawing Sheets

(51) Int. Cl.
  *A61B 6/03* (2006.01)
  *G06T 7/00* (2017.01)
(52) U.S. Cl.
  CPC .............. *G06T 2207/10081* (2013.01); *G06T 2207/30104* (2013.01)

(56) References Cited

U.S. PATENT DOCUMENTS

| | | | |
|---|---|---|---|
| 2012/0041318 A1 | 2/2012 | Taylor | |
| 2015/0038860 A1 | 2/2015 | Fonte | |
| 2015/0086461 A1* | 3/2015 | Wang | C01D 15/00 423/306 |
| 2015/0092999 A1 | 4/2015 | Schmitt | |
| 2015/0262357 A1* | 9/2015 | Igarashi | G06T 7/0016 382/131 |
| 2015/0282765 A1 | 10/2015 | Goshen | |
| 2016/0157807 A1* | 6/2016 | Anderson | A61B 5/02158 600/427 |
| 2016/0206265 A1* | 7/2016 | Schmitt | A61B 6/5217 |
| 2016/0302750 A1* | 10/2016 | Nickisch | G16H 50/50 |
| 2016/0310019 A1* | 10/2016 | Fonte | A61B 5/02007 |
| 2017/0245821 A1* | 8/2017 | Itu | A61B 6/507 |

OTHER PUBLICATIONS

Nickisch H. et al.,"Learning Patient-Specific Lumped Models for Interactive Coronary Blood Flow Simulations", Medical Image Computing and Computer-Assisted Intervention—MICCAI 2015:18th International Conference, LNCS, vol. 9350, pp. 433-441, 2015.

Freiman M. et al., "Improving CCTA-Based Lesions' Hemodynamic Significance Assessment by Accounting for Partial Volume Modeling in Automatic Coronary Lumen Segmentation", Medical Physics, vol. 44, issue 3, pp. 1040-1049, 2017.

Zheng Y. et al., "Robust and Accurate Coronary Artery Centerline Extraction in CTA by Combining Model-Driven and Data-Driven Approaches," Med Image Comput Assist Interv. 2013;16(Pt 3):74-81.

Ecabert O. et al., "Segmentation of the Heart and Great Vessels in CT Images Using a Model-Based Adaptation Framework," Medical Image Analysis, vol. 15, issue 6, Dec. 2011, pp. 863-876.

Rodes-Cabau J. et al., "Importance of Diffuse Atherosclerosis in the Functional Evaluation of Coronary Stenosis in the Proximal-Mid Segment of a Coronary Artery by Myocardial Fractional Flow Reserve Measurements", American Journal of Cardiology, vol. 108, issue 4, Aug. 15, 2011, pp. 483-490.

\* cited by examiner

STANDARDIZED CORONARY ARTERY DISEASE METRIC

FIELD OF THE INVENTION

The following generally relates to determining a coronary artery disease metric and more particularly to standardizing the coronary artery disease metric to a predetermined reference or common location along the coronary artery, and is described with particular application fractional to flow reserve-computed tomography (FFR-CT), but is also amenable to x-ray FFR (xFFR), instantaneous wave-free ratio (iFR), and the like.

BACKGROUND OF THE INVENTION

Fractional flow reserve (FFR) is an invasive measure in the cardiac catheterization laboratory (Cath Lab) to quantify, via an FFR index, the hemodynamic significance of a coronary lesion due to calcified or soft plaque. The index indicates the functional severity of a coronary stenosis that is calculated from pressure measurements made during coronary arteriography and is defined as the distal blood pressure (behind a stenosis) relative to the proximal pressure (close to the ostium) under hyperemic conditions. As such, the FFR index expresses the maximal flow down a vessel in the presence of a stenosis compared to the maximal flow in the hypothetical absence of the stenosis. The FFR value is a number between 0 and 1, where a value 0.50 indicates that a given stenosis causes a 50% drop in blood pressure. The established clinical threshold for functionally significance is 0.8 i.e. lesions with smaller FFR value should be treated.

An invasive FFR procedure requires insertion of a catheter into the femoral or radial arteries and advancement of the catheter to the stenosis where a sensor at the tip of the catheter senses pressure, temperature, and flow across the stenosis, during conditions promoted by various agents that affect vessel geometry, compliance and resistance, and/or other characteristics. A non-invasive approach (FFR-CT) estimates an FFR index from CT image data of the heart (e.g., from contrast enhanced coronary computed tomography angiography, CCTA) through computational fluid dynamic (CFD) simulations in which blood flow and pressure through the coronaries are simulated. This includes using CCTA image data to derive a geometrical model of the coronary tree and determine boundary conditions therefrom for the simulation.

In general, the blood pressure behind a stenosis (the distal blood pressure) drops with increased distance from the end of the stenosis. For example, due to friction laws, pressure measurements at more distal locations will yield smaller values as compared to pressure measurements at less distal locations, and this effect is more severe with smaller vessels than with larger vessels. As a consequence, an FFR value will depend on the location along the coronary artery where the FFR value is computed. As such, FFR values are not readily comparable across patients, clinicians, healthcare facilities, etc., e.g., due to differences/inconsistencies with regards to the locations selected by the clinicians for performing the FFR measurement.

SUMMARY OF THE INVENTION

Aspects described herein address the above-referenced problems and others.

In one aspect, a computing system includes a computer readable storage medium with computer executable instructions, including a biophysical simulator, and a reference location, and a processor configured to the biophysical simulator and simulate a reference FFR value at a predetermined location along a segmented coronary vessel indicated by the reference location. In another aspect, a computer readable storage medium encoded with computer readable instructions, which, when executed by a processor of a computing system, causes the processor to simulate a reference FFR value at a predetermined location along a segmented coronary vessel indicated by a predetermined reference location. In another aspect, a method including simulating a reference FFR value at a predetermined location along a segmented coronary vessel indicated by a predetermined reference location.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
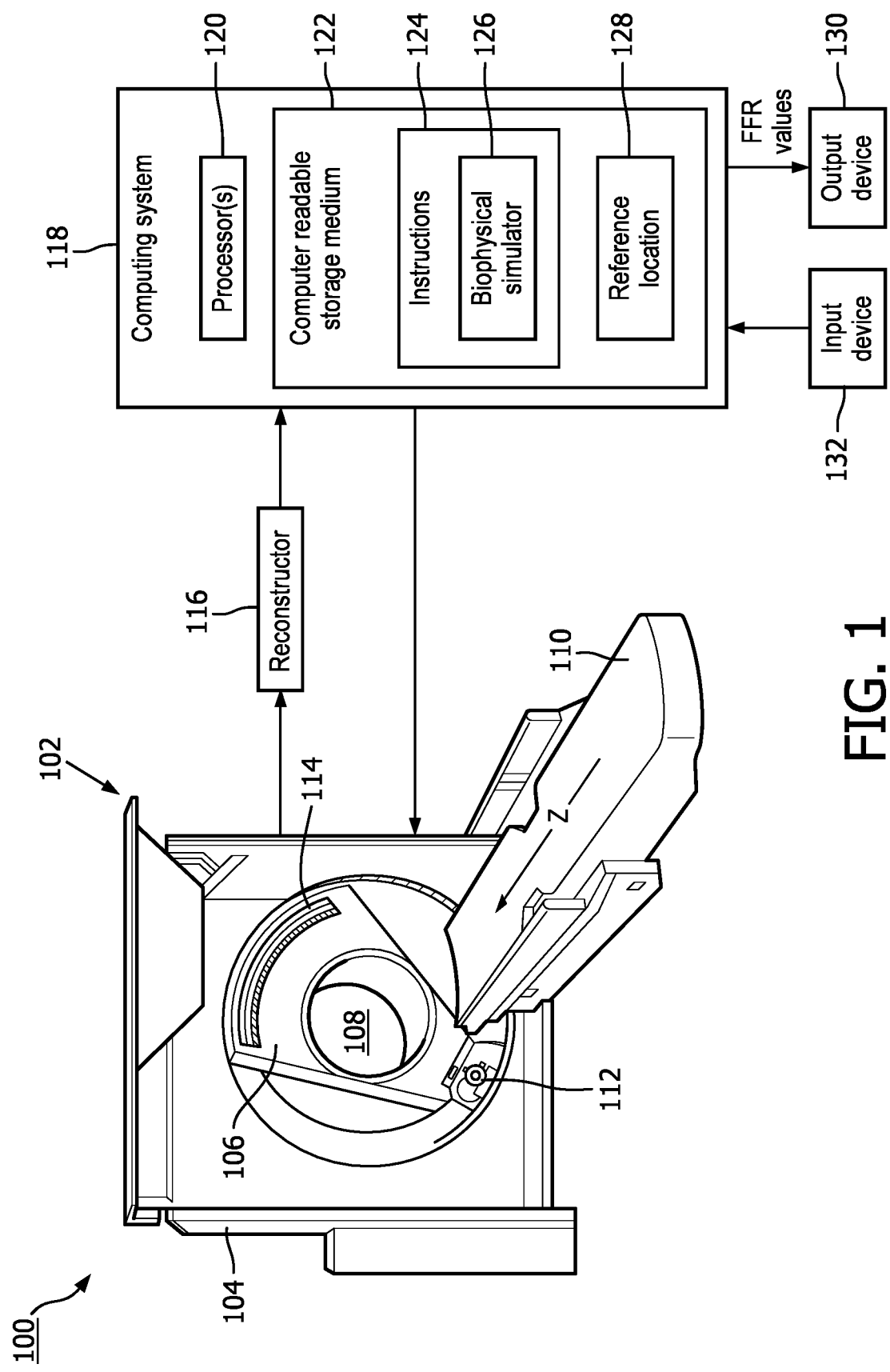
FIG. 1 schematically illustrates an example system that includes a computing system with a biophysical simulator and a reference location, and an imaging system.

FIG. 1 schematically illustrates a system 100 including an imaging system 102 such as a CT scanner. In a variation, the imaging system 102 includes an X-ray apparatus. The imaging system 102 includes a generally stationary gantry 104 and a rotating gantry 106, which is rotatably supported by the stationary gantry 104 and rotates around an examination region 108 about a z-axis. A subject support 110, such as a couch, supports an object or subject in the examination region 108.

A radiation source 112, such as an x-ray tube, is rotatably supported by the rotating gantry 106, rotates with the rotating gantry 106, and emits radiation that traverses the examination region 108. A radiation sensitive detector array 114 subtends an angular arc opposite the radiation source 112 across the examination region 1088. The radiation sensitive detector array 114 detects radiation traversing the examination region 108 and generates an electrical signal(s) (projection data) indicative thereof. A reconstructor 116 reconstructs the projection data, generating volumetric image data indicative of a scanned portion of a subject or object located in the examination region 108.

The system 100 further includes a computing system 118, which, in this example, serves as an operator console. The console 118 includes a processor 120 (e.g., a microprocessor, a central processing unit, etc.) and a computer readable storage medium 122, which excludes transitory medium, and includes non-transitory medium such as a physical memory device, etc. The console 118 further includes a human readable output device(s) 130 such as a monitor, and an input device(s) 132 such as a keyboard, mouse, etc.

The computer readable storage medium 122 includes instructions 124, for at least a biophysical simulator 126, and includes a predetermined reference location 128. The reference location 128 can be static or programmable. The processor 120 is configured to execute the instructions 124 and/or software that allows the operator to interact with and/or operate the scanner 102 via a graphical user interface (GUI) or otherwise. The processor 120 may additionally, or alternatively, execute a computer readable instruction(s) carried by a carrier wave, a signal and/or other transitory medium.

In a variation, the biophysical simulator 126 and the predetermined reference location 128 are part of another computing system, which is separate from the console 118 and the system 100. In this instance, the other computing system is similar to the console 118 in that it includes a processor, computer readable storage medium, an input device, and an output device, but it does not include the software that allows the operator to interact with and/or operate the scanner 102.

The biophysical simulator 126 is configured to determine an FFR value from cardiac image data. This includes an FFR value at a standard location along a vessel, e.g., at the location indicated by the reference location 128. As described in greater detail below, the FFR value at the standard location can at least be determined: 1) with cardiac CT image data (e.g., from the imaging system 102 and/or other system) along with an FFR at a user specified point along the vessel, 2) from an angiogram and an invasive FFR measurement, and/or 3) cardiac CT image data and a previously simulated FFR value determined therefrom. The standardized FFR allows FFR values to be compared across patients independent of clinician, healthcare facility, etc., e.g., regardless of the clinician-specified location.

Figure 2:
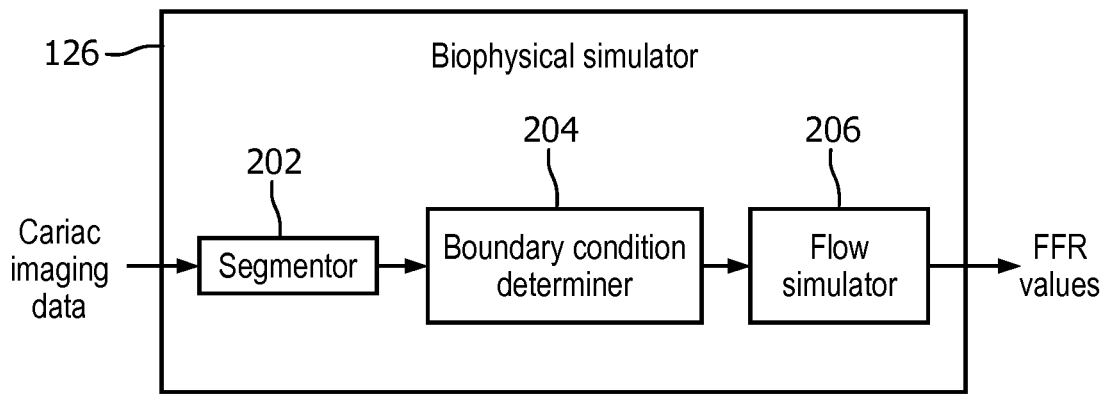
FIG. 2 schematically illustrates an example of the biophysical simulator.

FIG. 2 schematically illustrates an example of the biophysical simulator 126. In this example, the biophysical simulator 126 includes a segmentor 202, a boundary condition determiner 204, and a flow simulator 206. The biophysical simulator 126 receives, as input, image data from the imaging system 102, a data repository (e.g., a radiology information system (RIS), a picture and archiving system (PACS), etc.), and/or other apparatus, and outputs FFR values, including an FFR value at the reference location 128.

Figure 3:
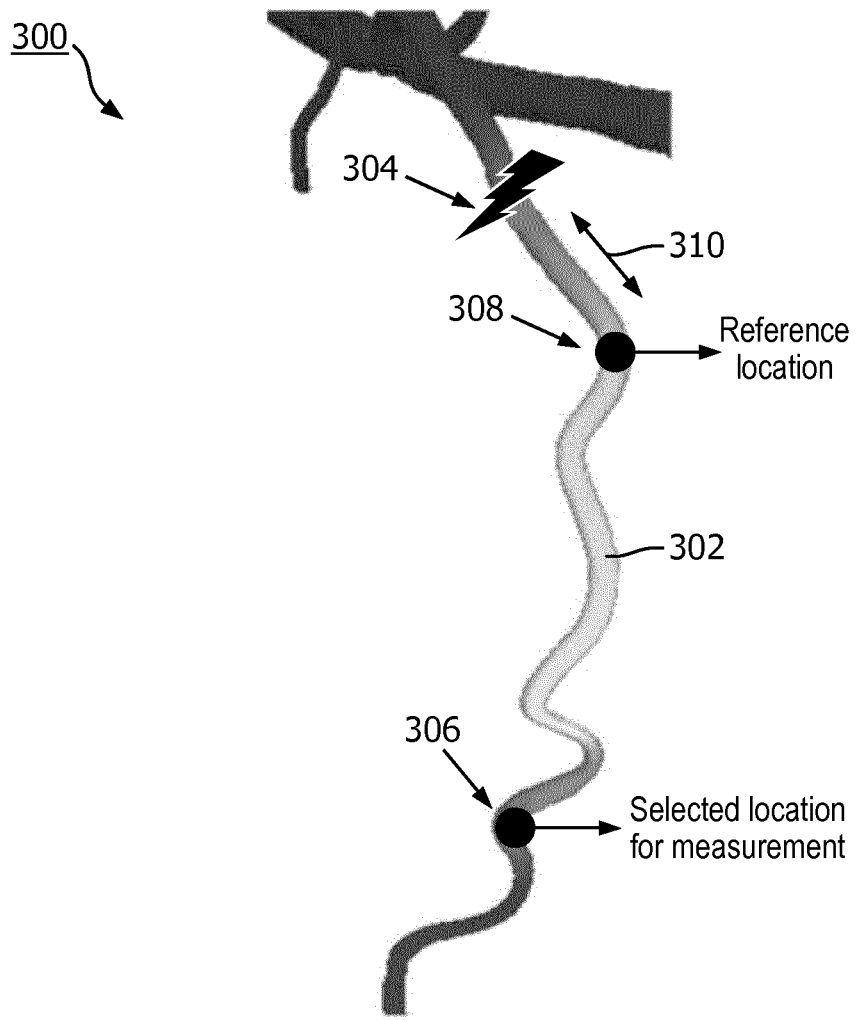
FIG. 3 schematically illustrates an example of a segmented coronary vessel showing a location of a stenosis, a user specified location for an FFR value, and a reference location for an FFR value.

The segmentor 202 employs a segmentation algorithm to segment the coronary tree from the image data. The segmentation can be performed automatically (e.g., machine learning, etc.) or semi-automatically (e.g., with user assistance). In one instance, the segmentation includes identifying and/or extracting coronary artery centerlines and/or lumen geometry (e.g., diameter, perimeter, cross-sectional area, etc.) therefrom. The segmentation can be based on voxel intensity, object shape, and/or other characteristics. FIG. 3 schematically illustrates a segmentation of a portion 300 of a coronary tree.

Examples of suitable approaches for extracting a coronary tree and cardiac chambers from image data are discussed in Zheng et al., "Robust and accurate coronary artery centerline extraction in CTA by combining model-driven and data-driven approaches," Med Image Comput Assist Interv. 2013; 16(Pt 3):74-81, Ecabert et al., "Segmentation of the heart and great vessels in CT images using a model-based adaptation framework," Med Image Anal. 2011 December; 15(6):863-76, and Freiman et al., "Improving CCTA-based lesions' hemodynamic significance assessment by accounting for partial volume modeling in automatic coronary lumen segmentation," Med Phys. 2017 March; 44(3):1040-1049. Other approaches are also contemplated herein.

The boundary condition determiner 204 determines boundary conditions for a simulation of blood flow in vessels from coronary tree segmentation. With one approach, a parametric lumped model is employed. The model includes a centerline representation using nonlinear resistances, with elements indicating inflow and outflow boundary conditions, and elements representing tree segment transfer functions, which include a series of linear and nonlinear resistance elements reflecting vessel geometry (e.g., diameter, perimeter, cross-sectional area, etc.) and/or hydraulic effects.

An example of a lumped model is discussed in Nickisch, et al., "Learning Patient-Specific Lumped Models for Interactive Coronary Blood Flow Simulations," in Medical Image Computing and Computer-Assisted Intervention—MICCAI 2015: 18th International Conference, LNCS, Vol. 9350, 2015, vol. 9350, pp. 433-441. An example of deriving boundary conditions is described in EP14174891.3, filed Jun. 30, 2014, and entitled "Enhanced Patient's Specific Modelling For FFR-CT," which is incorporated herein by reference in its entirety. Other approaches are also contemplated herein.

The flow simulator 206 performs a flow simulation with the boundary conditions and generates FFR values along the segmented coronary tree. The output FFR values include an FFR value at a user specified location along the vessel and an FFR value at the location identified by the reference location 128. For instance, in FIG. 3, a segmented vessel 302 includes a stenosis 304. The stenosis 304 can be identified in the segmented coronary tree, e.g., by a location corresponding to a greatest narrowing of an inner wall of the vessel (e.g., decreasing vessel radius or diameter), e.g., using an edge detection algorithm, evaluating voxel intensity values, etc.

A location 306 represents a user selected location for an FFR value. The user can specify the locations, e.g., via the input device 132, e.g., by "clicking" with a mouse or the like on a specific location on the segmented coronary tree. A reference location 308 indicates the location specified by the pre-determined reference location 128. In one instance, the pre-determined reference location 128 indicates the reference location 308 is a particular distance 310 downstream from an end of the stenosis. The end can be determined from radius or diameter measurements from the image data. In one instance, the distance 310 is a constant (e.g., 10 mm). In another instance, the distance 310 is a function of vessel geometry (e.g., 3×radius of portion of vessel before the stenosis 304 (healthy vessel). Other distances are also contemplated.

Flow simulations can be done, e.g., using a CFD and/or other approach. Examples of computing FFR values are described in US 2015/0092999 A1, filed May 10, 2013, and entitled "Determination of a fractional flow reserve (FFR) value for a stenosis of a vessel," US 2015/0282765 A1, filed Oct. 24, 2013, and entitled "Fractional flow reserve (FFR) index," which are incorporated herein by reference in their entireties. The output of the biophysical simulator 126 includes the FFR value at a user specified location 306 and the FFR value at the location 308. The values can be displayed via the output device 130 along with indicia indicating the location of each. In one instance, this includes superimposing the values over a graphical representation of the coronary tree, e.g., as sown in FIG. 3.

Figure 4:
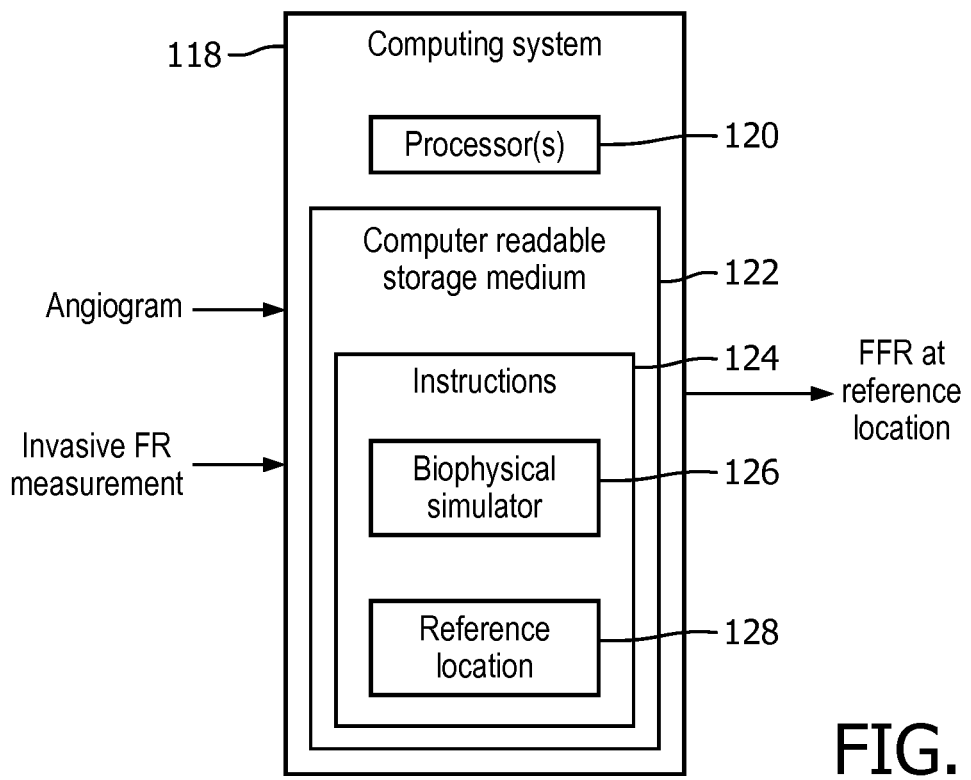
FIG. 4 schematically illustrates an example computing system, with the biophysical simulator and the reference location, configured to process an invasive FFR measurement and an angiogram.

FIG. 4 schematically illustrates an example in which the computing system 118 is separate from the system 100 and not a console of the imaging system 102. In this example, the computing system 118 receives, as input, an invasive FFR measurement and an angiogram used when taking the corresponding pressure measurement. The angiogram is segmented to extract the coronary tree, as described herein and/or otherwise. The angiogram is also analyzed to determine a location of a tip of the wire supporting the pressure sensor used to take the pressure measurement. In one instance, this is achieved by evaluating voxel intensity values in the angiogram.

The biophysical simulator 126, using segmented coronary tree, the determined location, and the invasive FFR measurement, determines model boundary conditions that would result in a simulation that would produce an FFR value at the determined location that is the same as the invasive FFR measurement value. For this, the same simulation pipeline for determining FFR values can be used, except an FFR value at a particular location is used to determine the boundary conditions. The simulation can then be performed with these boundary conditions to simulate FFR values along the entire vessel, and an FFR value at location specified by the reference location 128 can be determined. The FFRs can be displayed as discussed herein with numerical and/or graphical indicia indicating the corresponding locations on the segmented coronary tree.

Figure 5:
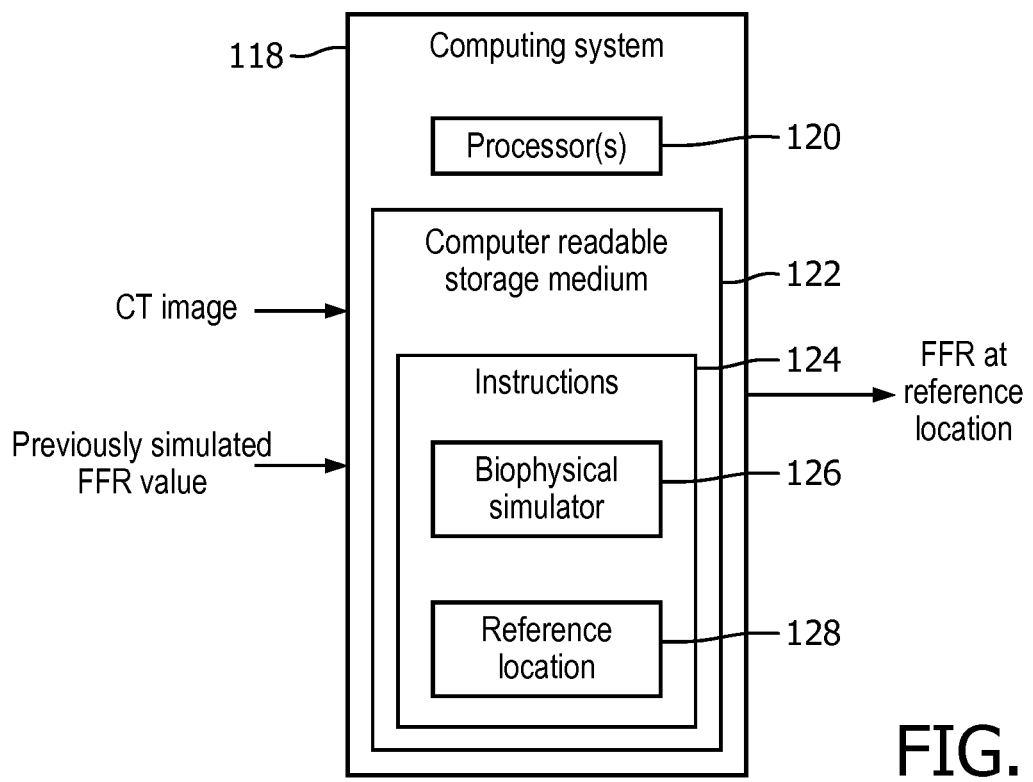
FIG. 5 schematically illustrates an example computing system, with the biophysical simulator and the reference location, configured to process a simulated FFR measurement and a CT image.

FIG. 5 schematically illustrates another example in which the computing system 118 is separate from the system 100 and not a console of the imaging system 102. In this example, the computing system 118 receives, as input, a previously simulated FFR value, and the image data used to simulate the FFR value. The biophysical simulator 126 segments the coronary tree from the image data, determines model boundary conditions, and simulates FFR values along the coronary tree. The previously simulated FFR value is mapped to a location on the coronary tree based on the simulated FFR values along the coronary tree and translated to the reference location. The FFRs can be displayed as discussed herein with numerical and/or graphical indicia indicating the corresponding locations on the segmented coronary tree.

FIGS. 1-5 described example that use FFR as a measure of a functional significance of coronary artery disease. In a variation, the approach described herein can also be applied to instantaneous wave-free ratio (iFR) and/or other measures. Generally, iFR is performed under rest, as opposed to FFR, using pressure wires that are passed distal to the coronary stenosis and isolates a specific period in diastole, called the wave-free period, and computes a ratio of distal coronary pressure to a pressure observed in the aorta over this period.

Figure 6:
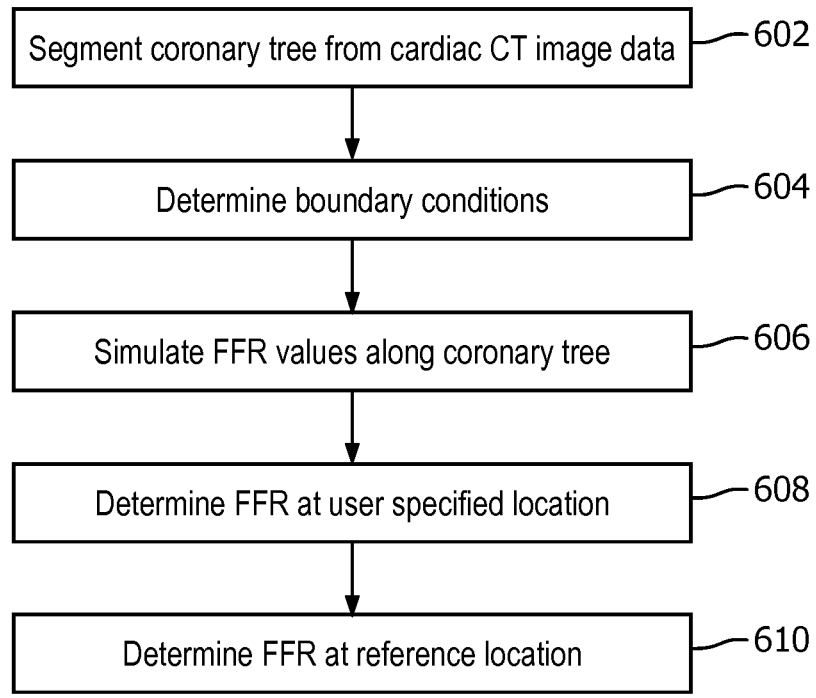
FIG. 6 illustrates an example method in accordance with an embodiment herein.

FIG. 6 illustrates an example method in accordance with an embodiment described herein.

At 602, a coronary tree is segmented from cardiac CT image data.

At 604, boundary conditions are determined therefrom for a flow simulation.

At 606, a flow simulation is performed with the boundary conditions to simulate FFR values along the coronary tree.

At 608, a simulated FFR value is determined at a user specified location along the coronary tree from the simulated FFR values.

At 610, another simulated FFR value is determined at the reference location 128 along the coronary tree from the simulated FFR values.

As described herein, the simulated FFRs can be displayed with numerical and/or graphical indicia indicating the corresponding locations on the segmented coronary tree.

Figure 7:
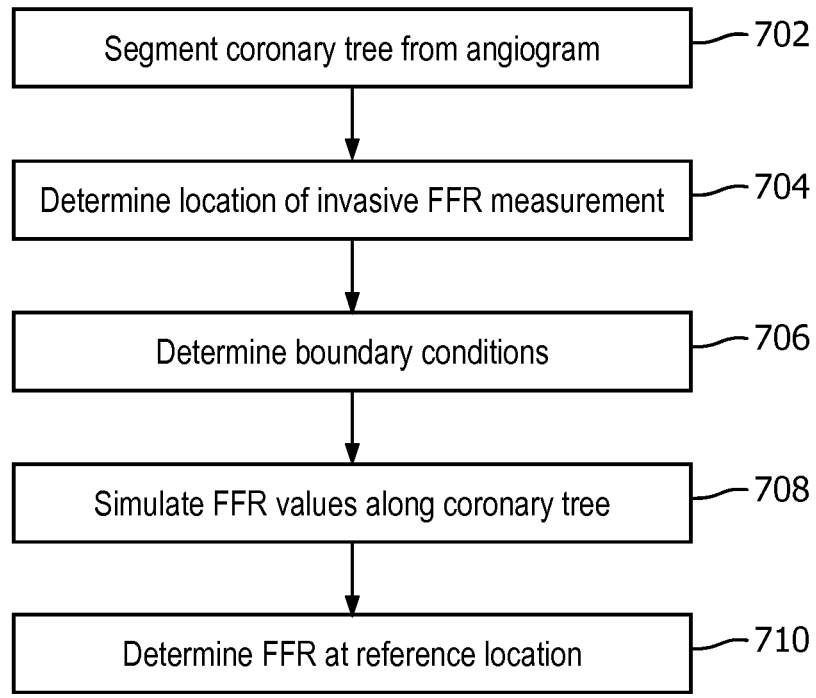
FIG. 7 illustrates another example method in accordance with an embodiment herein.

FIG. 7 illustrates another example method in accordance with an embodiment described herein.

At 702, a coronary tree is segmented from the angiogram.

At 704, a location of an invasive FFR measurement along the segmented coronary tree is determined from the angiogram.

At 706, boundary conditions are determined from the segmented coronary tree, the invasive FFR measurement, and the determined location.

At 708, a flow simulation is performed with the boundary conditions to simulate FFR values along the coronary tree.

At 710, a simulated FFR value is determined at the reference location 128 along the coronary tree from the simulated FFR values along the coronary tree.

As described herein, the simulated and invasive FFRs can be displayed with numerical and/or graphical indicia indicating the corresponding locations on the segmented coronary tree.

Figure 8:
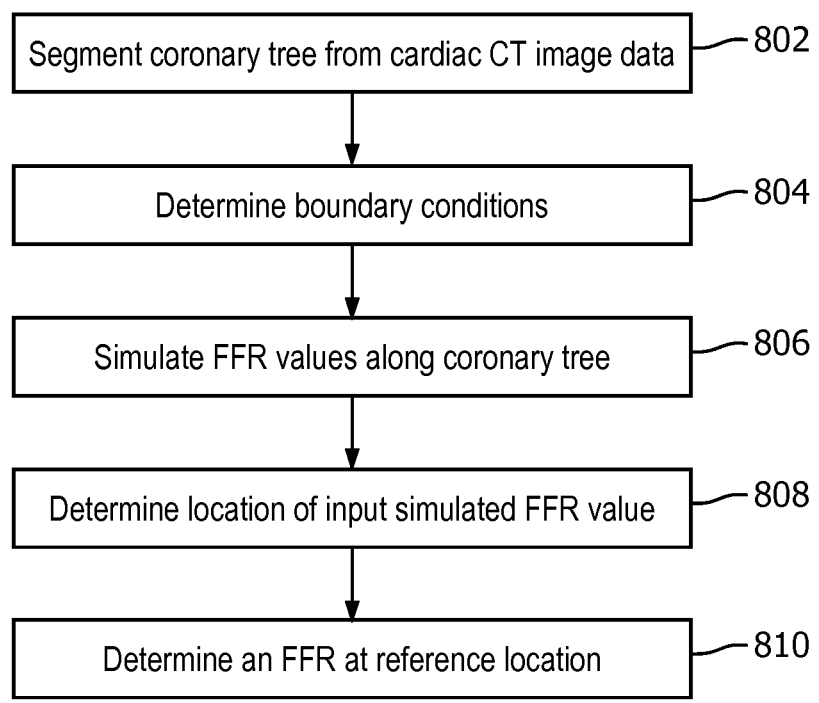
FIG. 8 illustrates another example method in accordance with an embodiment herein.

FIG. 8 illustrates another example method in accordance with an embodiment described herein.

At 802, a coronary tree is segmented from CT image data.

At 804, boundary conditions are determined from the segmented coronary tree.

At 806, a flow simulation is performed with the boundary conditions to simulate FFR values along the coronary tree.

At 808, a location of an input previously simulated FFR value is determined from the simulated FFR values along the coronary tree.

At 810, a simulated FFR value is determined at the predetermined reference location 128 along the coronary tree from the simulated FFR values along the coronary tree.

As described herein, the simulated and previously simulated FFRs can be displayed with numerical and/or graphical indicia indicating the corresponding locations on the segmented coronary tree.

The above may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium, which is not computer readable storage medium. Furthermore, it is to be appreciated that the ordering of the acts is not limiting. As such, other orderings are contemplated herein. In addition, one or more acts may be omitted and/or one or more additional acts may be included.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computing system, comprising:
    a computer readable storage medium with computer executable instructions; and
    processor circuitry configured to:
        segment a coronary vessel;
        identify a stenosis in the coronary vessel;
        identify a distal end of the stenosis;
        measure a geometric value associated with a coronary vessel geometry;
        determine, based on the measured geometric value, a distance which is a constant or a function of the measured geometric value;
        determine, based on the determined distance and the distal end, a reference location which is a location in the coronary vessel at the determined distance from the distal end; and
        determine a Fractional Flow Reserve (FFR) value at the reference location.

2. The computing system of claim 1, wherein the processor circuitry is further configured to:
    segment the coronary vessel from cardiac computed tomography image data,
    determine boundary conditions for a flow simulation based thereon,
    perform the flow simulation with the boundary conditions producing simulated FFR values along the segmented coronary vessel, and
    determine a selected FFR value of the simulated FFRs that corresponds to a user specified location along the coronary vessel.

3. The computing system of claim 2, wherein the processor circuitry is further configured to:
    visually present the FFR value at the reference location and the selected FFR value with indicia indicating the reference location and the user specified location.

4. The computing system of claim 3, wherein the processor circuitry is further configured to:
    visually present the segmented coronary vessel with the FFR value at the reference location and the selected FFR value superimposed thereover and the indicia indicating the reference location and the user specified location.

5. The computing system of claim 1, wherein the processor circuitry is further configured to:
    segment the coronary vessel from an angiogram,
    determine an invasive FFR measurement location on the segmented coronary vessel where an invasive FFR measurement was taken, and
    determine boundary conditions such that a simulated FFR value at the invasive FFR measurement location is same as the invasive FFR measurement.

6. The computing system of claim 5, wherein the processor circuitry is further configured to:
    perform a simulation with the determined boundary conditions to simulate FFR values along the segmented coronary vessel, and
    translate the invasive FFR measurement to the reference location to determine the FFR value at the reference location.

7. The computing system of claim 6, wherein the processor circuitry is further configured to:
    visually present the FFR value at the reference location and the invasive FFR measurement along with indicia indicating the reference location and the invasive FFR measurement location.

8. The computing system of claim 7, wherein the processor circuitry is further configured to:
    visually present the segmented coronary vessel with the FFR value at the reference location and the invasive FFR measurement superimposed thereover and with the indicia indicating the reference location and the invasive FFR measurement location.

9. The computing system of claim 1, wherein the processor circuitry is further configured to:
    segment the coronary vessel from cardiac computed tomography image data,
    determine boundary conditions for a flow simulation based thereon,
    perform the flow simulation with the boundary conditions producing simulated FFR values along the segmented coronary vessel,
    identify a location of an input previously simulated FFR value by matching the input previously simulated FFR value to one of the simulated FFR values along the segmented coronary vessel, and
    determine the FFR value at the reference location from the simulated FFRs.

10. The computing system of claim 9, wherein the processor circuitry is further configured to:
    visually present the reference and input previously simulated FFR values respectively with indicia indicating the reference location and the location of the input previously simulated FFR value.

11. The computing system of claim 10, wherein the processor circuitry is further configured to:
    visually present the segmented coronary vessel with the reference and input previously simulated FFR values superimposed thereover and with the indicia indicating the reference location and the location of the input previously simulated FFR value.

12. The computing system of claim 1,
    wherein the measuring of the geometric value includes measuring a diameter of the segmented coronary vessel proximal to the stenosis;
    wherein the determining of the distance includes determining, based on the measured diameter, a distance of a multiple of the measured diameter.

13. The computing system of claim 1, wherein the processor circuitry is further configured to:
    translate an FFR value at a user specified location along the coronary vessel to the reference FFR value at the reference location.

14. A non-transitory computer readable storage medium encoded with computer readable instructions which, when executed by processor circuitry, cause the processor circuitry to perform a method comprising:
    segmenting a coronary vessel;
    identifying a stenosis in the coronary vessel;
    identifying a distal end of the stenosis;
    measuring a geometric value associated with a coronary vessel geometry;
    determining, based on the measured geometric value, a distance which is a constant or a function of the measured geometric value;
    determining, based on the determined distance and the distal end, a reference location which is a location in the coronary vessel at the determined distance from the distal end; and
    determining a Fractional Flow Reserve (FFR) value at the reference location.

15. The non-transitory computer readable storage medium of claim 14, wherein the processor circuitry segments the coronary vessel from cardiac computed tomography image data, determines boundary conditions for a flow simulation based thereon, performs the flow simulation with the boundary conditions producing simulated FFR values along the segmented coronary vessel, and determines a selected simulated FFR value of the simulated FFRs that corresponds to a user specified location along coronary vessel.

16. The non-transitory computer readable storage medium of claim 14, wherein the processor circuitry segments the coronary vessel from an angiogram, determines a location of the segmented coronary vessel where an invasive FFR measurement was taken, determines boundary conditions which compute a simulated FFR value for the determined location that is the same as the invasive FFR measurement based on the invasive FFR measurement and the determined location, performs the flow simulation with the boundary conditions producing simulated FFR values along the segmented coronary vessel, determines the FFR value at the reference location from the simulated FFRs.

17. The non-transitory computer readable storage medium of claim 14, wherein the processor segments the coronary vessel from cardiac computed tomography image data, determines boundary conditions for a flow simulation based thereon, performs the flow simulation with the boundary conditions producing simulated FFR values along the segmented coronary vessel, identifies a location of an input previously simulated FFR value along the segmented coronary vessel with the simulated FFR values, determines the FFR value at the reference location from the simulated FFRs.

18. A method, comprising:
    segmenting a coronary vessel;
    identifying a stenosis in the coronary vessel;
    identifying a distal end of the stenosis;
    measuring a geometric value associated with a coronary vessel geometry;
    determining, based on the measured geometric value, a distance which is a constant or a function of the measured geometric value;
    determining, based on the determined distance and the distal end, a reference location which is a location in the coronary vessel at the determined distance from the distal end; and
    determining a Fractional Flow Reserve (FFR) value at the reference location.

19. The method of claim 18, further comprising:
    segmenting the coronary vessel from cardiac computed tomography image data;
    determining boundary conditions for a flow simulation based thereon;
    performing the flow simulation with the boundary conditions producing simulated FFR values along the segmented coronary vessel;
    visually presenting a selected simulated FFR value for a user specified location with indicia indicating the user specified location;
    determining the FFR value at the reference location from the simulated FFRs; and
    visually presenting the FFR value at the reference location with indicia indicating the reference location.

20. The method of claim 18, further comprising:
    segmenting the coronary vessel from an angiogram;
    determining a location of the segmented coronary vessel where an invasive FFR measurement was taken from the angiogram; and
    determining boundary conditions for a flow simulation to compute a simulated FFR value for the determined location that is the same as the invasive FFR measurement based on the invasive FFR measurement and the determined location;
    performing the flow simulation with the boundary conditions producing simulated FFR values along the segmented coronary vessel;
    determining the FFR value at the reference location from the simulated FFRs; and
    visually presenting at least the FFR value at the reference location with indicia indicating the reference location.

21. The method of claim 18, further comprising:
    segmenting the coronary vessel from cardiac computed tomography image data;
    determining boundary conditions for a flow simulation based thereon;
    performing the flow simulation with the boundary conditions producing simulated FFR values along the segmented coronary vessel;
    identifying a location of an input previously simulated FFR value with the simulated FFR values along the segmented coronary vessel;
    translating the input previously simulated FFR value to the FFR value at the reference location with the simulated FFRs; and
    visually presenting at least the FFR value at the reference location with indicia indicating the reference location.

* * * * *